United States Patent
Koh

(10) Patent No.: US 8,571,652 B2
(45) Date of Patent: Oct. 29, 2013

(54) ADAPTIVE DETERMINATION OF PATIENT SPECIFIC OPTIMAL AV DELAY DURING ELEVATED HEART RATES BASED ON CARDIAC OUTPUT MEASUREMENTS

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 901 days.

(21) Appl. No.: 12/701,816

(22) Filed: Feb. 8, 2010

(65) Prior Publication Data
US 2011/0196440 A1    Aug. 11, 2011

(51) Int. Cl.
*A61N 1/362* (2006.01)
(52) U.S. Cl.
USPC .................................... 607/9; 607/15; 607/17
(58) Field of Classification Search
USPC ............................................. 607/2, 9, 17–24
See application file for complete search history.

(56) References Cited

U.S. PATENT DOCUMENTS

2006/0173503 A1 *    8/2006    Baynham .......................... 607/9

FOREIGN PATENT DOCUMENTS

WO        2008039110 A1      4/2008

* cited by examiner

*Primary Examiner* — Carl H Layno
*Assistant Examiner* — Paula J Stice

(57) ABSTRACT

Adaptively creating a table of optimal, patient-specific atrioventricular (AV) delays for a an implantable medical device (IMD) begins as the IMD detects the patient entering a target heart rates within a defined range of elevated heart rates. On detection, the device begins testing AV delays by pacing the heart at a number of different AV delays. The IMD selects the optimal AV delay based on a comparison of measurements of cardiac output obtained during each delay's test pacing period. The optimal AV delay corresponds to the one which resulted in the highest cardiac output. The device selects this optimal AV delay and stores it in an AV delay table on the device. The process continues as the device detects the patient entering the other target heart rates in order to complete the table.

20 Claims, 12 Drawing Sheets

ADAPTIVE DETERMINATION OF PATIENT SPECIFIC OPTIMAL AV DELAY DURING ELEVATED HEART RATES BASED ON CARDIAC OUTPUT MEASUREMENTS

FIELD OF THE DISCLOSURE

The present disclosure relates, in general, to cardiac pacing and, more particularly, to adaptive determination of patient-specific optimal atrioventricular (AV) delay during elevated heart rates based on cardiac output measurements.

BACKGROUND

An implantable medical device (IMD), such as a pacemaker and/or implantable cardioverter-defibrillator (ICD), regulates or synchronizes the beating of the heart with electrical impulses, delivered by electrodes contacting the heart muscles. Some IMDs include a number of different sensors and logic allowing them to monitor the rate and rhythm of the heart as well as to measure various cardiac surrogates that provide information on the operation of the heart.

One of the primary purposes of implantable medical devices (IMDs) is to maintain an adequate heart rate, either because the heart's natural pacemaker is inadequate, or there are problems with the heart's electrical conduction system. However, maintaining an adequate heart rate is not always a simple matter of firing off the heart to beat at a certain time. It often includes the complex synchronization of the individual movements and processes that make up each stage of a typical heart beat. As measurements are made and analyzed by the IMD, electrical therapies may be delivered when the performance or synchronization of the heart varies from some pre-defined measurement of normal operation.

One important area of cardiac performance is atrioventricular (AV) delay. AV delay is the delay that occurs in the synchronized operation of the left atrium and left ventricle. As blood fills the left atrium, the mitral valve, between the left atrium and the left ventricle, remains closed. When the left ventricle relaxes, the mitral valve opens causing the left ventricle to fill while the left atrium contracts, thus, pushing blood into the relaxed left ventricle. As the atrium ceases its contraction, the mitral valve closes. The aortic valve opens allowing the ventricle to push blood into the aorta when the ventricle contracts. The AV delay is the delay between the atrium ceasing its contraction and the ventricle beginning its contraction to push the blood into the aorta. In a synchronized operation, the delay is such that the atrium stops contracting after an adequate ventricular fill before the ventricle begins to contract.

FIG. 3A is an echocardiogram illustrating a cardiac signal graph 330. The cardiac signal graph 330 provides an indication of the AV delay in a given cardiac cycle through measurement of a mitral inflow signal 300 and an aortic outflow signal 301. The mitral inflow signal 300 measures the blood flow that occurs through the mitral valve between the atrium and ventricle during atrial contraction and ventricular relaxation. The aortic outflow signal 301 measures the blood flow that occurs through the aortic valve during ventricular contraction. A transition point 302 is present between the full flow periods of the mitral inflow signal 300 and aortic outflow signal 301. The presence of this transition point 302 indicates that the atrium ceased contraction and the ventricle began contraction in an efficient sequence that allowed maximum ventricular fill before contraction. Such operation indicates a properly optimal AV delay.

The AV delay is not a static period. It changes depending on the heart rate. For example, during exercise, the heart rate rises to deliver blood to the more active parts of the body. The AV delay that was optimal for the person at rest cannot now be optimal for the person exercising. The faster heart rate requires a faster ventricular fill, which requires a faster atrial contraction. Therefore, a resting AV delay will not be optimal with elevated heart rates. FIG. 3B is an echocardiogram illustrating a cardiac signal graph 331. The AV delay indicated by the cardiac signal graph 331 is too long for the presenting heart rate, i.e., a situation in which a resting AV delay could be present in an elevated heart rate. Observing the mitral inflow signal 300 and aortic outflow signal 301 in the cardiac signal graph 331, it can be seen that the two signals overlap without a defined transition point. The overlap means that blood is still flowing through the mitral valve, i.e., the atrium is still contracting and pushing blood, while blood is being pushed through the aortic valve, i.e., the ventricle is also contracting. With both the atrium and ventricle pushing, it is possible to experience regurgitation of blood from the ventricle back into the atrium through the mitral valve. This backflow of blood is referred to as mitral regurgitation (MR).

The cardiac signal graph 331 shows an AV delay that is too long for the particular heart rate. Thus, as the heart continues to beat faster, the atrium stays in a contracting state too long before the ventricle begins its contraction. The AV delay may also be too short for a given heart rate. FIG. 3C is an echocardiogram illustrating a cardiac signal graph 332. Here, instead of an optimal transition point, such as the transition point 302 (FIG. 3A), a transition gap 303 exists between the mitral inflow signal 300 and the aortic outflow signal 301. This relationship does not result in both the atrium and ventricle pushing at the same time, but does result in both being relaxed at the same time. This gap could result in an inadequate fill time for the ventricle, which would lead to inadequate blood flow. It could also result in MR as the atrium begins to refill with blood before the ventricle begins contracting, thus, lowering the pressure differential between the atrium and ventricle, which could allow the mitral valve to open slightly during ventricular contraction. Thus, optimization of AV delay for varying heart rates in IMD patients represents a complex task.

Moreover, the optimum AV delay for one patient at a given heart rate will typically not be the optimum AV delay for a different patient at the same given heart rate. FIG. 4 is an optimal AV delay graph 440 illustrating the optimal AV delays for a number of different patients. Each graphed collection of points represents the optimal AV delay for a given patient at three measured heart rates. A first observation of the optimal AV delay graph 440 would indicate that optimal AV delay does not follow any particular pattern between patients. Observing optimal AV delays for patients at the same heart rates also shows that the optimal AV delay is usually different. For example, points 400 and 401 represent optimal AV delays for two patients both having a heart rate of approximately 60 beats per minute (bpm). While the heart rates are the same, point 400 reflects an optimal AV delay of approximately 120 milliseconds (ms), while point 401 reflects an optimal AV delay of approximately 100 ms. Two additional measurements for these patients occur at points 402 and 403, at a heart rate of approximately 88 bpm each. At this heart rate, the optimal AV delay for the patient of points 400 and 402 is now approximately 100 ms, while the optimal AV delay for the patient of points 401 and 403 is now approximately 40 ms. The third measured points 404 and 405 complete the graphs of the two patients. While the general shape of these two graphs result in a similar shape, the relationship between the two is such that a series of AV delays would be difficult to universally select to optimally apply to both patients.

Existing methods for determining individualized AV delays generally have the patient come to a testing facility that has a stress test machine. As the patient performs the stress test, technicians monitor the patient's heart using an electrocardiography (ECG) machine or similar device. The optimal AV delay is usually calculated for each heart rate based on an optimization of the patient's interventricular (VV) delay. The technicians can then program the patient's IMD with the various AV delays optimized for the tested heart rates.

SUMMARY

Representative embodiments of the present teachings are directed to adaptively creating a table of optimal, patient-specific atrioventricular (AV) delays for a patient using an implantable medical device (IMD). The device generates a target range of elevated heart rates for the user by creating a histogram of heart rates over a particular period. A resting AV delay is also obtained as a starting point of the optimal delays associated with the patient's heart rates. As the device detects the patient entering any of the target heart rates within the range, the device begins testing AV delays by pacing the heart at a number of different AV delays. The device using this optimization process will select the optimal AV delay of the delays tested based on a comparison of measurements of cardiac output obtained during each delay's test pacing period. The optimal AV delay will correspond to the one which resulted in the highest or largest cardiac output. The device selects this optimal AV delay and stores it in an AV delay table on the device to be used the next time the patient enters the same target heart rate. The process continues as the device detects the patient entering the other target heart rates.

Additional representative embodiments of the present teachings are directed to methods that optimize AV delay in elevated heart rates. Such methods include measuring a heart rate from an IMD and pacing the heart using multiple, different AV delays. The pacing is performed responsive to the heart rate falling within a target range of elevated heart rates. The methods further include measuring a cardiac output of the heart during the pacing at each of the AV delays and selecting an optimal AV delay from the pacing at the tested AV delays. The optimal AV delay corresponds to one of the AV delays producing a highest cardiac output. The optimal AV delay and the heart rate are then stored in an optimal AV delay table on the IMD.

Further representative embodiments of the present teachings are directed to IMDs. Such IMDs include a heart rate sensor, at least one cardiac pacing lead, at least one cardiac output sensor, and a programmable microcontroller coupled to each of the leads and sensors. The programmable microcontroller controls operation of the IMD. The IMDs also include a memory coupled to the programmable microcontroller and an AV delay optimization feature module is stored on the memory. When executed by the programmable microcontroller, the AV delay optimization feature module configures the IMD to measure a heart rate of a heart associated with the device and to operate the cardiac pacing lead to pace the heart using multiple, different AV delays in response to the heart rate falling within a target range of elevated heart rates stored in an optimal AV table on the memory. The executing AV delay optimization feature additionally configures the IMD to operate the cardiac output sensor to measure a cardiac output of the heart during the pacing at each of the tested AV delays. The executing AV delay optimization feature further configures the IMD to select an optimal AV delay. The optimal AV delay corresponds to the AV delay that produces the highest cardiac output. The optimization feature then stores the optimal AV delay in AV delay table associated with the heart rate.

Still further representative embodiments of the present teachings are directed to systems that optimize AV delay in elevated heart rates. These systems include means for measuring a heart rate from an IMD and means, executable responsive to the heart rate falling within a target range of elevated heart rates, for pacing a heart using multiple, different AV delays. The systems further include means for measuring a cardiac output of the heart during the pacing at each of the tested AV delays, and means for selecting an optimal AV delay. The optimal AV delay corresponds to the AV delay that produces the highest cardiac output. The systems also have means for storing the optimal AV delay and the heart rate in an optimal AV delay table on the IMD.

The foregoing has outlined rather broadly the features and technical advantages of the present teachings in order that the detailed description of the teachings that follows may be better understood. Additional features and advantages of the teachings will be described hereinafter which form the subject of the claims of the teachings. It should be appreciated by those skilled in the art that the conception and specific embodiments disclosed may be readily utilized as a basis for modifying or designing other structures for carrying out the same purposes of the present teachings. It should also be realized by those skilled in the art that such equivalent constructions do not depart from the spirit and scope of the teachings as set forth in the appended claims. The novel features believed to be characteristic of the teachings, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present teachings.

BRIEF DESCRIPTION OF THE DRAWINGS

For a more complete understanding of the present disclosure, reference is now made to the following descriptions taken in conjunction with the accompanying drawings.

DETAILED DESCRIPTION

The following description includes the best mode presently contemplated for practicing the present teachings. The description is not to be taken in a limiting sense but is merely for the purpose of describing the general principles of the illustrative embodiments. The scope of the present teachings should be ascertained with reference to the claims. In the description that follows, like numerals or reference designators will refer to like parts or elements throughout.

Overview of Implantable Devices

Figure 1:
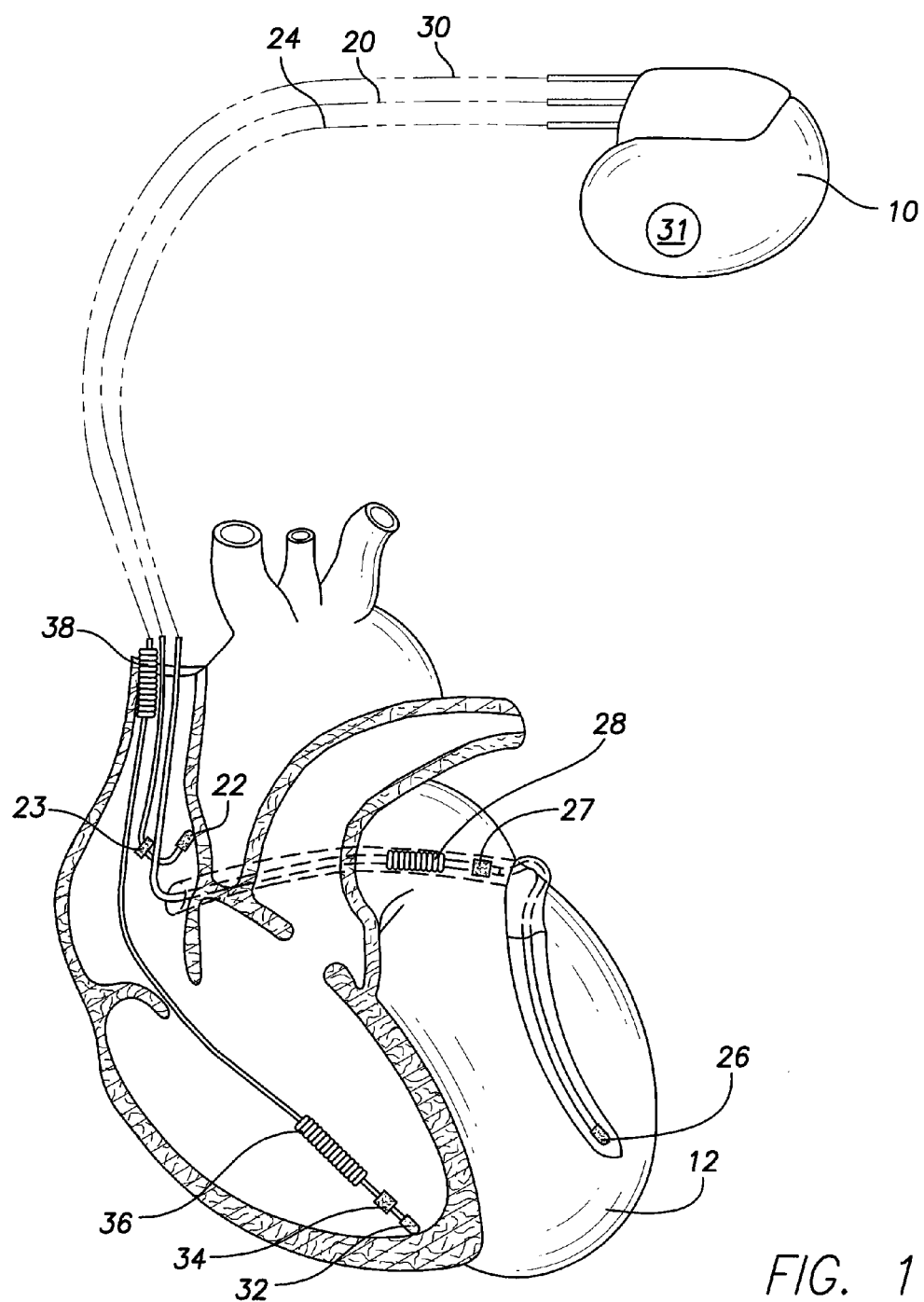
FIG. 1 is a diagram illustrating a stimulation device in electrical communication with the heart of a patient by way of three leads suitable for delivering multi-chamber stimulation and shock therapy.

With reference to FIG. 1, there is a stimulation device 10 in electrical communication with the heart 12 of a patient by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage, and an atrial ring electrode 23.

To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart so as to place the right ventricular tip electrode 32 in the right ventricular apex so the RV coil electrode 36 is positioned in the right ventricle and the SVC coil electrode 38 is positioned in the superior vena cava. Accordingly, the right ventricular lead 30 is capable of receiving cardiac signals, and delivering stimulation in the form of pacing and shock therapy to the right ventricle. To provide a "vibratory alert" signal (from a motor with an offset mass that can be provided in the device can), an additional electrode 31 can be provided in proximity to the device can.

Figure 2A:
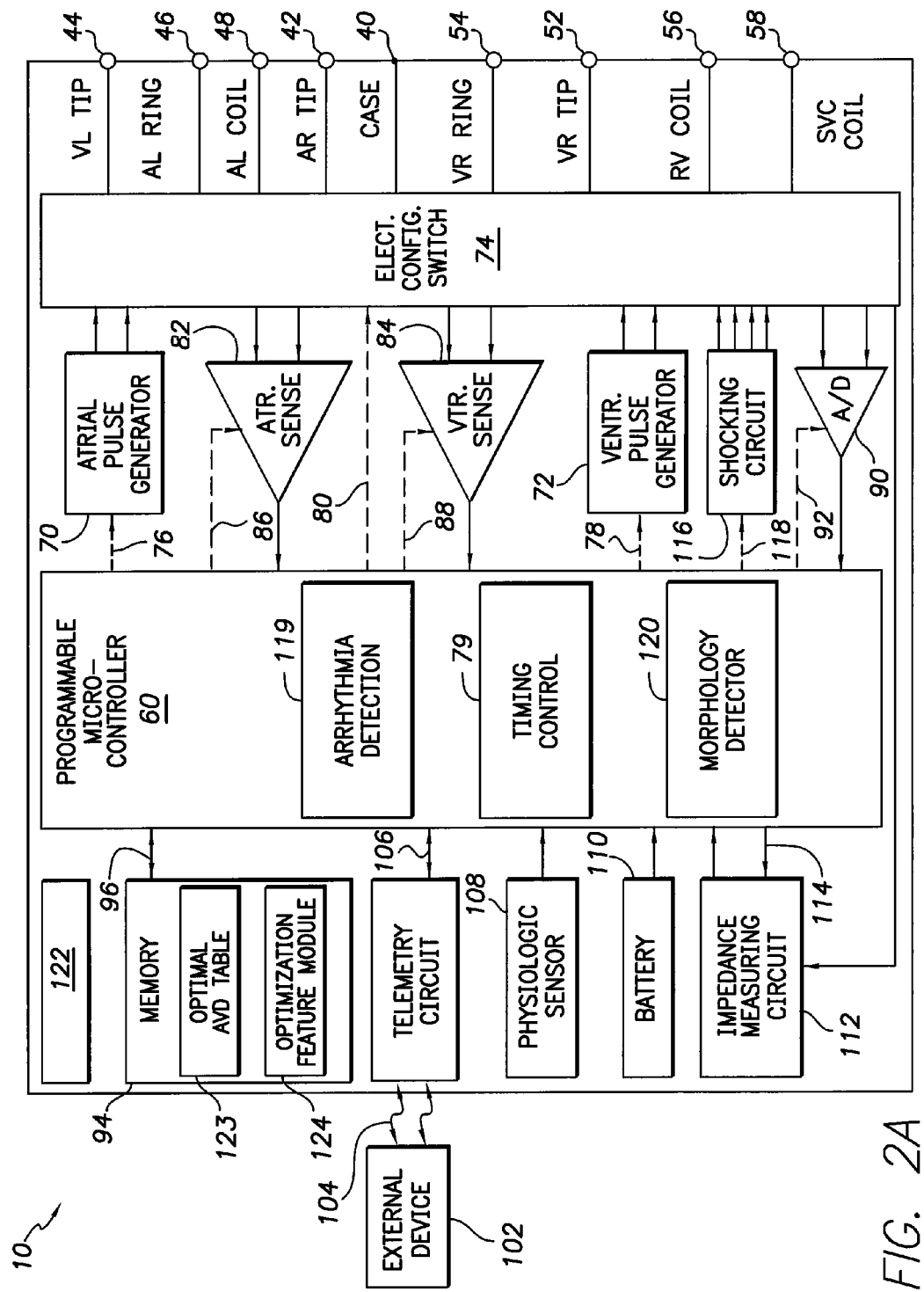
FIG. 2A is a simplified block diagram illustrating an implantable stimulation device configured as a system in which the various embodiments of the present teachings may operate.

As illustrated in FIG. 2A, a simplified block diagram is shown of the multi-chamber implantable stimulation device 10, which is capable of treating both fast and slow arrhythmias with stimulation therapy, including cardioversion, defibrillation, and pacing stimulation. The stimulation device 10 is configured as a system in which the various embodiments of the present teachings may operate. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2A, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, (FIG. 1) for shocking purposes. The housing 40 further includes a connector (not shown) having multiple terminals, 42, 44, 46, 48, 52, 54, 56 and 58 (shown schematically and, for convenience, the names of the electrodes to which they are connected are shown next to the terminals).

As such, to achieve right atrial sensing and pacing, the connector includes at least a right atrial tip terminal ($A_R$ TIP) 42 adapted for connection to the atrial tip electrode 22 (FIG. 1) and a right atrial ring ($A_R$ RING) electrode (not shown) adapted for connection to the right atrial ring electrode 23 (FIG. 1). To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26 (FIG. 1), the left atrial tip electrode 27 (FIG. 1), and the left atrial coil electrode 28 (FIG. 1), respectively. To support right chamber sensing, pacing and shocking, the connector further includes a right ventricular tip terminal ($V_R$ TIP) 52, a right ventricular ring terminal ($V_R$ RING) 54, a right ventricular shocking terminal (RV COIL) 56, and an SVC shocking terminal (SVC COIL) 58, which are adapted for connection to the right ventricular tip electrode 32 (FIG. 1), right ventricular ring electrode 34 (FIG. 1), the RV coil electrode 36 (FIG. 1), and the SVC coil electrode 38 (FIG. 1), respectively. To provide the "vibratory alert" signal, a vibratory alert unit 122 generates a signal for an additional terminal (not shown) for connection to the vibratory alert electrode 31 (FIG. 1). In one embodiment, the vibratory alert will alert the patient, and then a home monitor can be used to transfer the information associated with the alert from the device 10 to an attending medical professional, who can take the appropriate clinical action.

At the core of the stimulation device 10 is a programmable microcontroller 60, which controls the various modes of stimulation therapy. As is well known in the art, the microcontroller 60 (also referred to as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by program code stored in a designated block of the memory. The details of the design and operation of the microcontroller 60 are not critical to the present teachings. Rather, any suitable microcontroller 60 may be used that carries out the functions described. The use of microprocessor-based control circuits for performing timing and data analysis functions is well known in the art.

As shown in FIG. 2A, an atrial pulse generator 70 and a ventricular pulse generator 72 generate pacing stimulation pulses for delivery by the right atrial lead 20 (FIG. 1), the right ventricular lead 30 (FIG. 1), and/or the coronary sinus lead 24 (FIG. 1) via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 that controls the timing of such stimulation pulses (e.g., pacing rate, atrioventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., as is well known in the art. The switch 74 includes multiple switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20 (FIG. 1), the coronary sinus lead 24 (FIG. 1), and the right ventricular lead 30 (FIG. 1), through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers and may receive control signals 86, 88 from the controller 60. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, band pass filtering, and a threshold detection circuit, as known in the art, to selectively sense the cardiac signal of interest. The automatic gain control enables the device 10 to effectively address the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks).

Cardiac signals are also applied to the inputs of an analog-to-digital (ND) data acquisition system 90. The data acquisition system 90 is configured to acquire intra-cardiac electrogram (IEGM) signals, convert the raw analog data into a digital signal, and store the digital signals for later processing and/or telemetric transmission to an external device 102. The data acquisition system 90 is coupled to the right atrial lead 20 (FIG. 1), the coronary sinus lead 24 (FIG. 1), and the right ventricular lead 30 (FIG. 1) through the switch 74 to sample cardiac signals across any pair of desired electrodes. The controller 60 controls the data acquisition system via control signals 92.

The microcontroller 60 is further coupled to a memory 94 by a suitable data/address bus 96. The programmable operating parameters used by the microcontroller 60 are stored and modified, as required, in order to customize the operation of the stimulation device 10 to suit the needs of a particular patient. The memory 94 includes software modules, such as the AV optimization feature module 124 and the optimal AV delay table 123, which, when executed or used by the microcontroller 60, provide the operational functions of the implantable stimulation device 10. Additional operating parameters and code stored on the memory 94 define, for example, pacing pulse amplitude or magnitude, pulse duration, electrode polarity, rate, sensitivity, automatic features, arrhythmia detection criteria, and the amplitude, wave shape and vector of each shocking pulse to be delivered to the patient's heart within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, trans-telephonic transceiver, a diagnostic system analyzer, or even a cellular telephone. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In one embodiment, the stimulation device 10 further includes a physiologic sensor 108, commonly referred to as a "rate-responsive" sensor because it adjusts pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient.

The stimulation device additionally includes a battery 110, which provides operating power to all of the circuits shown in FIG. 2A. For the stimulation device 10, which employs shocking therapy, the battery 110 is capable of operating at low current drains for long periods of time, and is capable of providing high-current pulses (for capacitor charging) when the patient requires a shock pulse. The battery 110 also has a predictable discharge characteristic so that elective replacement time can be detected. In one embodiment, the device 10 employs lithium/silver vanadium oxide batteries. As further shown in FIG. 2A, the device 10 has an impedance measuring circuit 112 enabled by the microcontroller 60 via a control signal 114.

The stimulation device 10 detects the occurrence of an arrhythmia and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the heart 12 through at least two shocking electrodes, and as shown in this embodiment, selected from the left atrial coil electrode 28 (FIG. 1), the RV coil electrode 36 (FIG. 1), and/or the SVC coil electrode 38 (FIG. 1). As noted above, the housing 40 may function as an active electrode in combination with the RV coil electrode 36 (FIG. 1), or as part of a split electrical vector using the SVC coil electrode 38 (FIG. 1) or the left atrial coil electrode 28 (FIG. 1) (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

The microcontroller 60 includes a morphology detector 120 for tracking various morphological features within electrical cardiac signals, including intervals between polarization events, elevations between polarization events, durations of polarization events and amplitudes of polarization events. The microcontroller 60 also includes an arrhythmia detection control 119 that analyzes the sensed electrical signals to determine whether or not arrhythmia is being experienced.

Figure 2B:
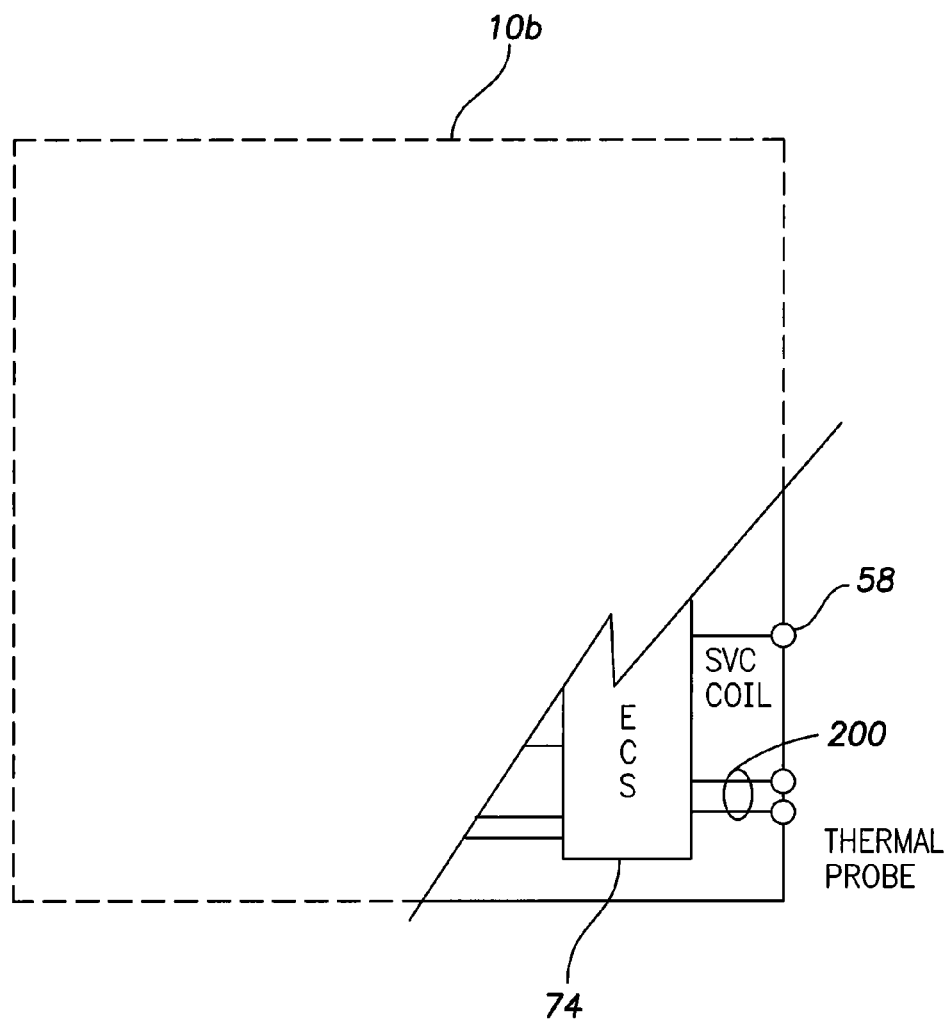
FIG. 2B is a block diagram illustrating partial detail of a stimulation device configured as a system in which the various embodiments of the present teachings may operate.

FIG. 2B is a block diagram illustrating partial detail of a stimulation device 10b configured as a system in which the various embodiments of the present teachings may operate. The stimulation device 10b includes each of the features illustrated with regard to the stimulation device 10 (FIG. 2A), and, as such, the majority of detail is hidden in FIG. 2B for the sake of clarity. The illustrated portion of the stimulation device 10b provides the addition of a thermal probe 200 connected to the electrical configuration switch 74, along with the remaining contacts, such as the SVC coil 58. The thermal probe 200 allows the stimulation device 10b to conduct cardiac output measurements through thermal dilution.

Figure 2C:
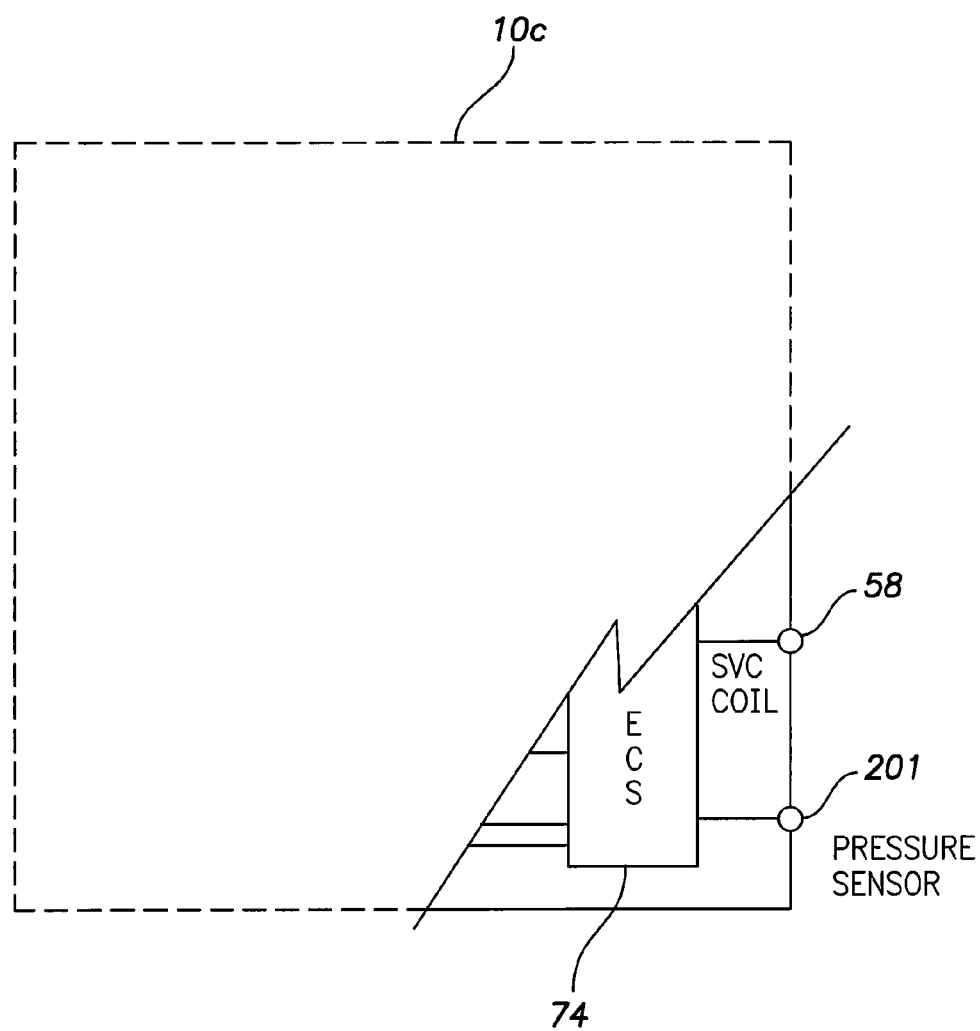
FIG. 2C is a block diagram illustrating partial detail of a stimulation device configured as a system in which the various embodiments of the present teachings may operate.
Figure 3A:
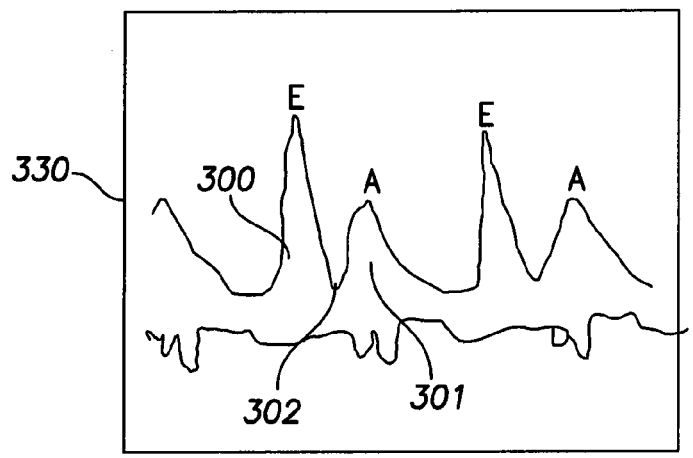
FIG. 3A is an echocardiogram illustrating a cardiac signal graph.
Figure 3B:
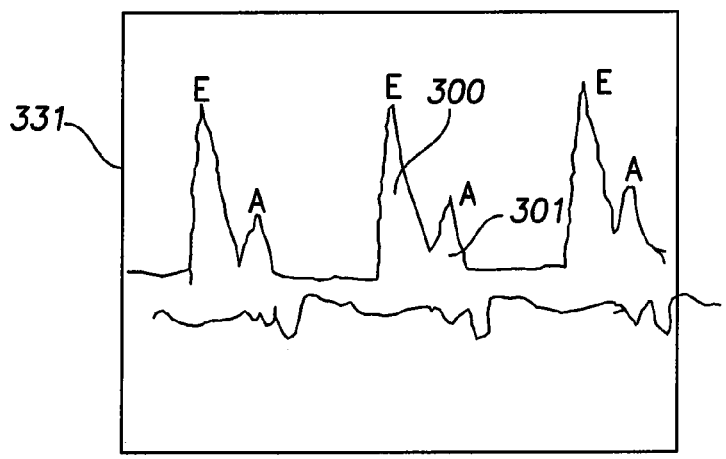
FIG. 3B is an echocardiogram illustrating another cardiac signal graph.
Figure 3C:
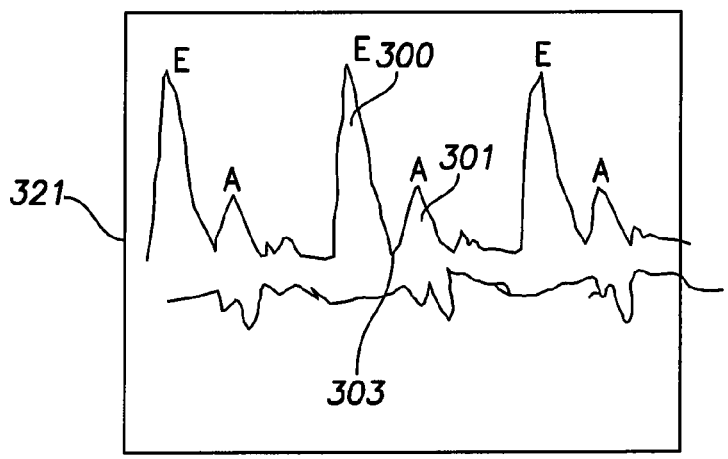
FIG. 3C is an echocardiogram illustrating another cardiac signal graph.
Figure 4:
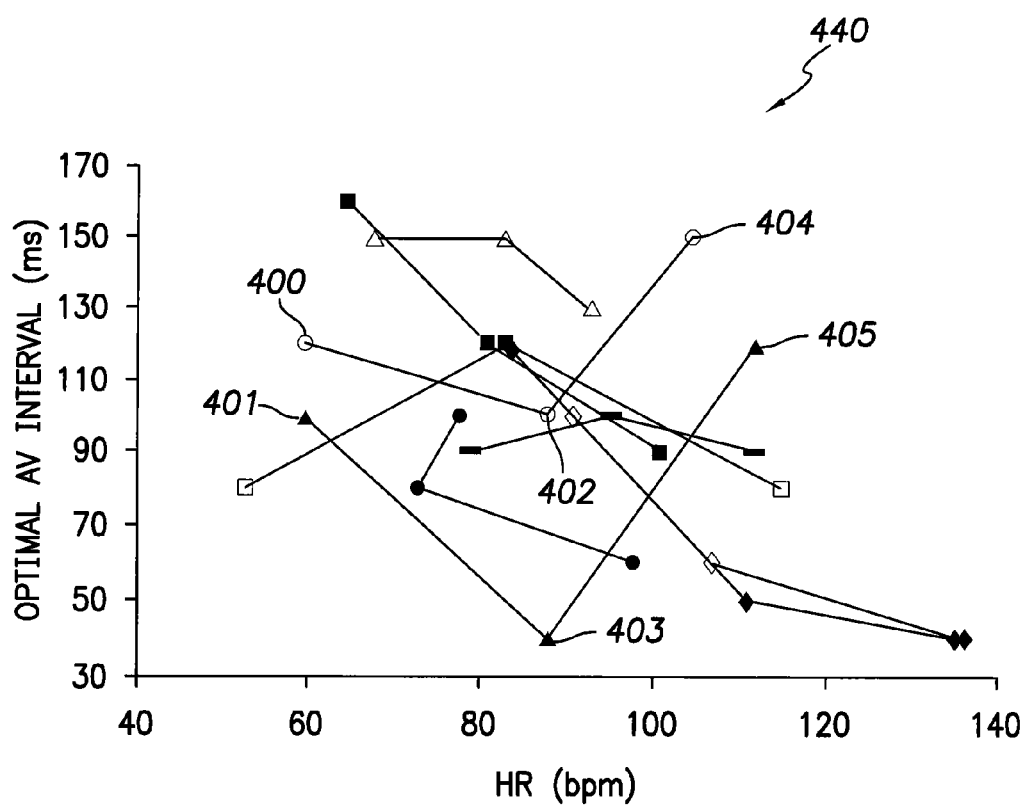
FIG. 4 is an optimal AV delay graph illustrating the optimal AV delays for a number of different patients.

FIG. 2C is a block diagram illustrating partial detail of a stimulation device 10c configured as a system in which the various embodiments of the present teachings may operate. The stimulation device 10c includes each of the features illustrated with regard to the stimulation device 10 (FIG. 2A), and, as such, the majority of detail is hidden in FIG. 2C for the sake of clarity. The illustrated portion of the stimulation device 10c provides the addition of a pressure sensor 201 connected to the electrical configuration switch 74, along with the remaining contacts, such as the SVC coil 58. The pressure sensor 201 allows the stimulation device 10c to conduct cardiac output measurements using atmospheric pressure readings in blood vessels and calculations based on principles of fluid dynamics. The operation of these devices will be described below with reference to the remaining figures.

The remaining figures, flow charts, graphs and other diagrams illustrate the operation and novel features of the stimulation device 10 as configured in accordance with exemplary embodiments of the present teachings. In the flow chart, the various process steps are summarized in individual "blocks." Such blocks describe specific actions or decisions made or carried out as the process proceeds. Where a microcontroller (or equivalent) is employed, the flow chart provides the basis for an "AV delay optimization process" that may be used by such a microcontroller (or equivalent) to adaptively determine patient-specific optimal AV delays for elevated heart rates. Those skilled in the art may readily write such a program based on the flow chart and other descriptions presented herein.

Determining Patient-Specific Optimal AV Delays

For purposes of the present teachings, the various implantable devices capable of performing the embodiments of the present teachings, such as ICDs, dual chamber ICDs, pacemakers, CRT devices, and the like, will be referred to generically as "implantable medical devices," (IMDs). An IMD monitors and records the heart rates experienced by the patient over a given period of time. Based on this information, a range of target heart rates can be established for which to find optimal AV delays. Because each patient will have a different optimal AV delay for every target heart rate, a table is defined that stores the optimal AV delay associated with each particular target heart rate within the range. This table is stored in memory on the IMD. When a new heart rate is detected, the IMD access the table to find the associated optimal AV delay. The IMD then uses this optimal AV delay to pace the patient's heart.

In order to fill this table with the optimal AV delays, the IMD adaptively performs tests at different AV delays as the patient reaches each target heart rate in the table. The IMD selects the best of the tested AV delays based on a measurement of cardiac output during each of the tested AV delays. This selected optimal AV delay is then stored in the AV delay table associated with the particular target heart rate. Over time, an optimal AV delay is selected for each of the target heart rates within the patient's range. Also over time, the IMD will perform updates of the optimal delays in order to maintain an accurate set of delays for a patient, whose heart function may be deteriorating or improving.

It should be noted that the IMD measures the cardiac output in various numbers of available ways including measurement of aortic arch flow surrogates, such as cardiac impedance, thermodilution, pressure sensing, and the like.

Figure 5:
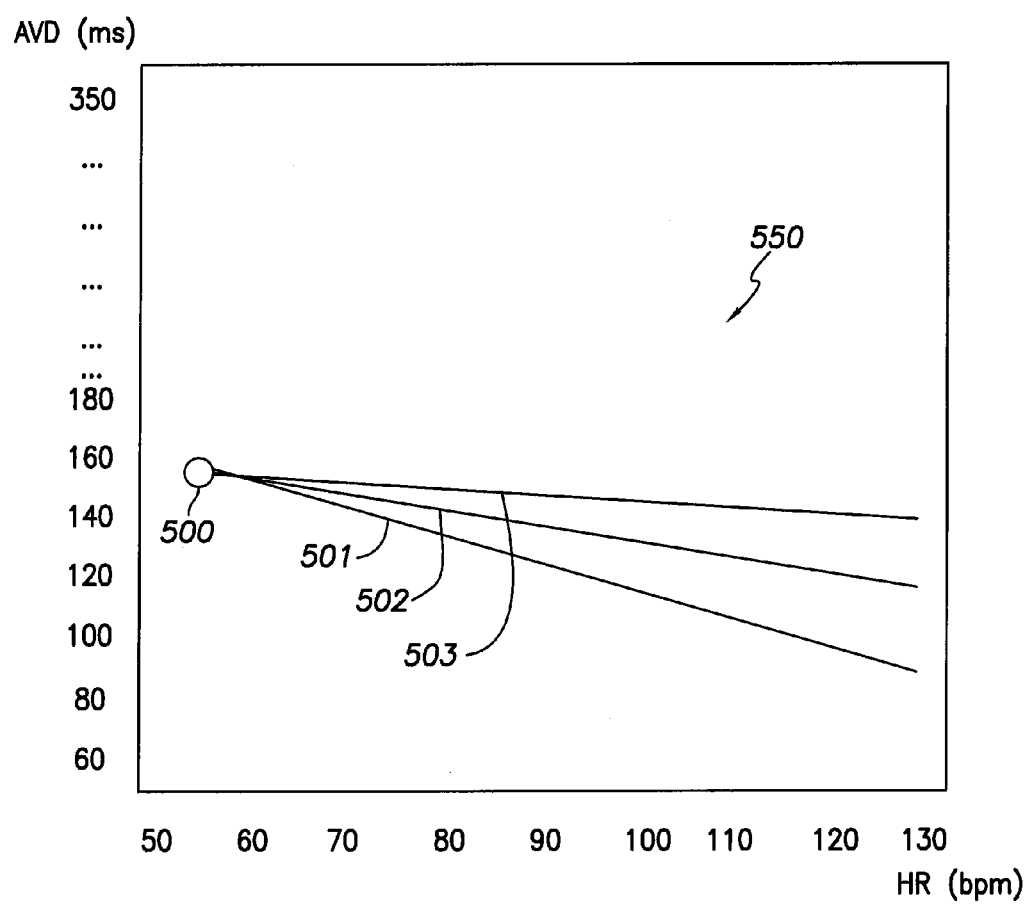
FIG. 5 is an AV delay chart illustrating a set of standard AV delays.

The IMDs that provide systems in which the various embodiments of the present teachings may operate include numerous testing and measurement functions such as those that can measure and record the patient's heart rates, AV delays, and cardiac output. Prior to beginning the optimization procedure, the IMD generates a series of standard AV delays. These standard AV delay values are default non patient specific values, or are values determined based on an echocardiogram analyzed during a periodic visit with a physician our other qualified personnel. FIG. 5 is an AV delay chart 550 illustrating a set of standard AV delays. The AV delay chart 550 begins at the resting state of the patient with a resting AV delay 500. Three levels of AV delay are then plotted for elevated heart rates, a low AV delay set 501, a medium AV delay set 502, and a high AV delay set 503. As the optimization process begins, the IMD detects the patient at one of the target heart rates that needs an optimized AV delay. Using the standard set of AV delays plotted in the AV delay chart 550, the IMD switches into test mode and begins by pacing the heart based on the low AV delay corresponding to the target heart rate along the low AV delay set 501. The IMD measures the cardiac output at this low AV delay. The IMD continues by testing the cardiac output of a medium AV delay from the medium AV delay set 502 and a high AV delay from the high AV delay set 503. Comparing the three cardiac output measurements, the IMD selects the AV delay that resulted in the highest cardiac output. This AV delay is then stored in the optimized AV delay table. Each time the patient reaches one of the other target heart rates, the IMD will perform this test to find the optimal AV delay corresponding to that particular heart rate.

It should be noted that the embodiment of the present teachings for which the AV delay chart 550 is used is only one example of the multiple, different AV delays that may be used. In additional and/or alternative embodiments of the present teachings, more or fewer than three sets of test AV delays may be used.

Figure 6:
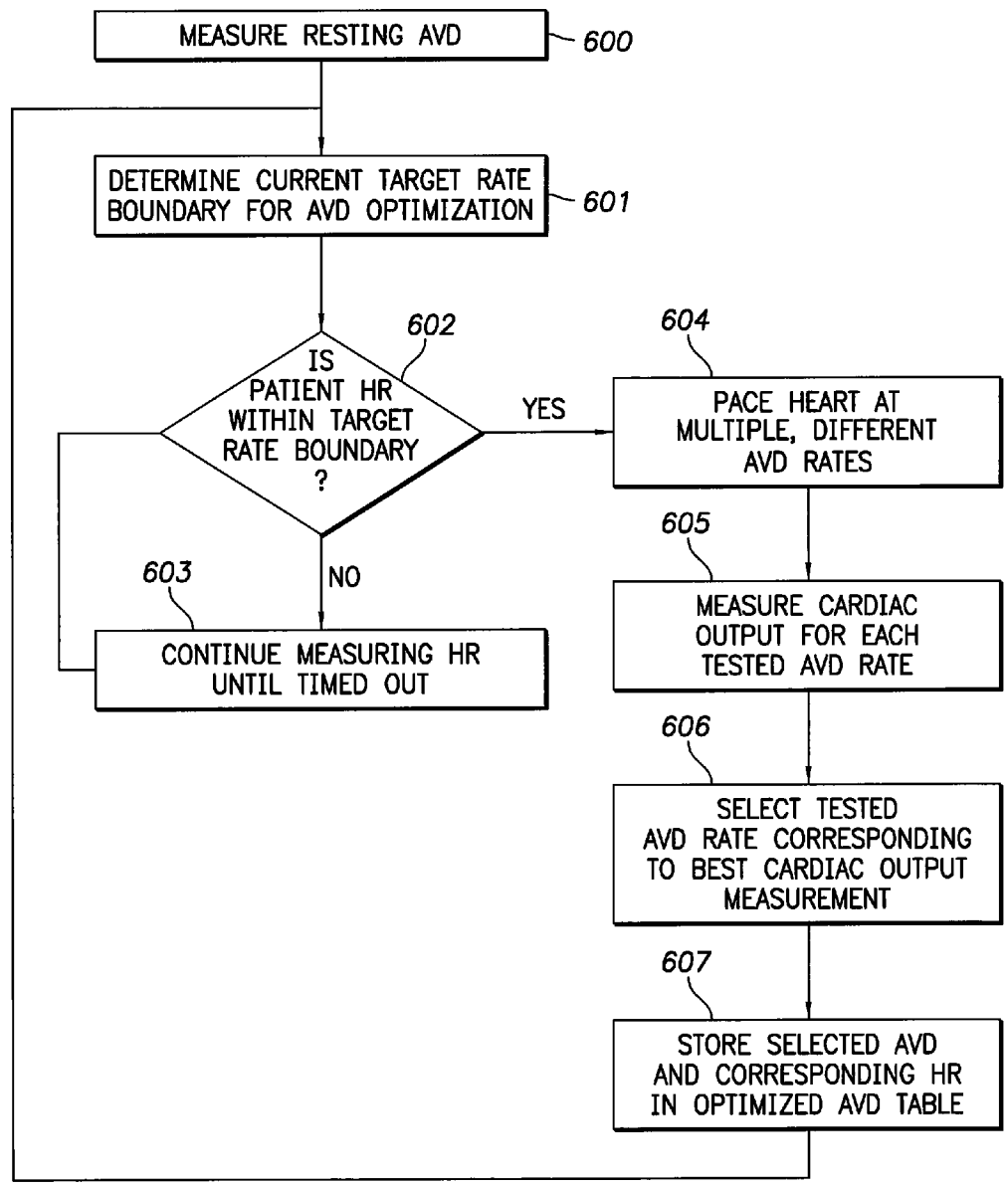
FIG. 6 is a functional block diagram illustrating example functional blocks that occur in one embodiment of the present teachings.

FIG. 6 is a functional block diagram illustrating example functional blocks that occur in one embodiment of the present teachings. In block 600, the resting AV delay is measured. This measurement may be taken directly by the IMD or by an external testing machine, after which the resting AV delay would be programmed into the IMD. In block 601, the current target rate boundary is determined for AV delay optimization. Through measurement of the patient's heart rate, a determination is made, in block 602, whether the patient's heart rate is within the target rate boundary. If not, then, in block 603, the patient's heart rate keeps getting measured until timed out. Each subsequent measurement is again submitted to the determination in block 602.

If the patient's heart rate is within the target rate boundary, then, in block 604, the heart is paced at multiple, different AV delay rates. The cardiac output of the heart is measured, in block 605, for each of the tested AV delay rates. In block 606, the tested AV delay rate that corresponds to the best or highest cardiac output measurement is selected. This selected AV delay rate and its corresponding heart rate are then stored, in block 607, into the optimized AV delay table. The process begins again with the determination of the current target rate boundary in block 601.

Measuring the cardiac output of a heart being paced at any given AV delay may be accomplished through numerous well known methods. The term cardiac output often refers to the volume of blood pumped from the heart over a minute. It may be calculated by determining the stroke volume, which is the amount of blood pumped by the ventricle during each contraction/relaxation cycle, and multiplying it by the bpm heart rate. Stroke volume is equal to the difference between the end diastolic volume (EDV) (the volume of blood in the ventricle at its most full) and the end systolic volume (ESV) (the volume of blood remaining in the ventricle after it completes contraction). The cardiac output measured for purposes of the various embodiments of the present teachings is not limited to a measurement that results in some volume for each minute, as provided in the standard definition of cardiac output. Instead, the various embodiments of the present teachings measure cardiac output by measuring or detecting some indicator of the amount of blood being pumped from a heart, whether that measurement reflects the amount of blood flowing over a given period of time or the amount of blood flowing over a given event, such as a ventricular contraction, cardiac cycle, or the like.

Stroke volume is often calculated by measuring a surrogate level representing aortic arch blood flow. One such method measures the cardiac impedance during a ventricular contraction/relaxation cycle. The impedance measuring circuit 112 (FIG. 2A) provides the hardware and circuitry to take such measurements. In one embodiment, the cardiac impedance is measured from the SVC coil electrode to the IMD housing. With reference to the present teachings, when an IMD detects a patient's heart rate is within the target rate boundary for AV delay optimization, cardiac impedance is measured during the pacing at each of the different test AV delay rates.

Figure 7:
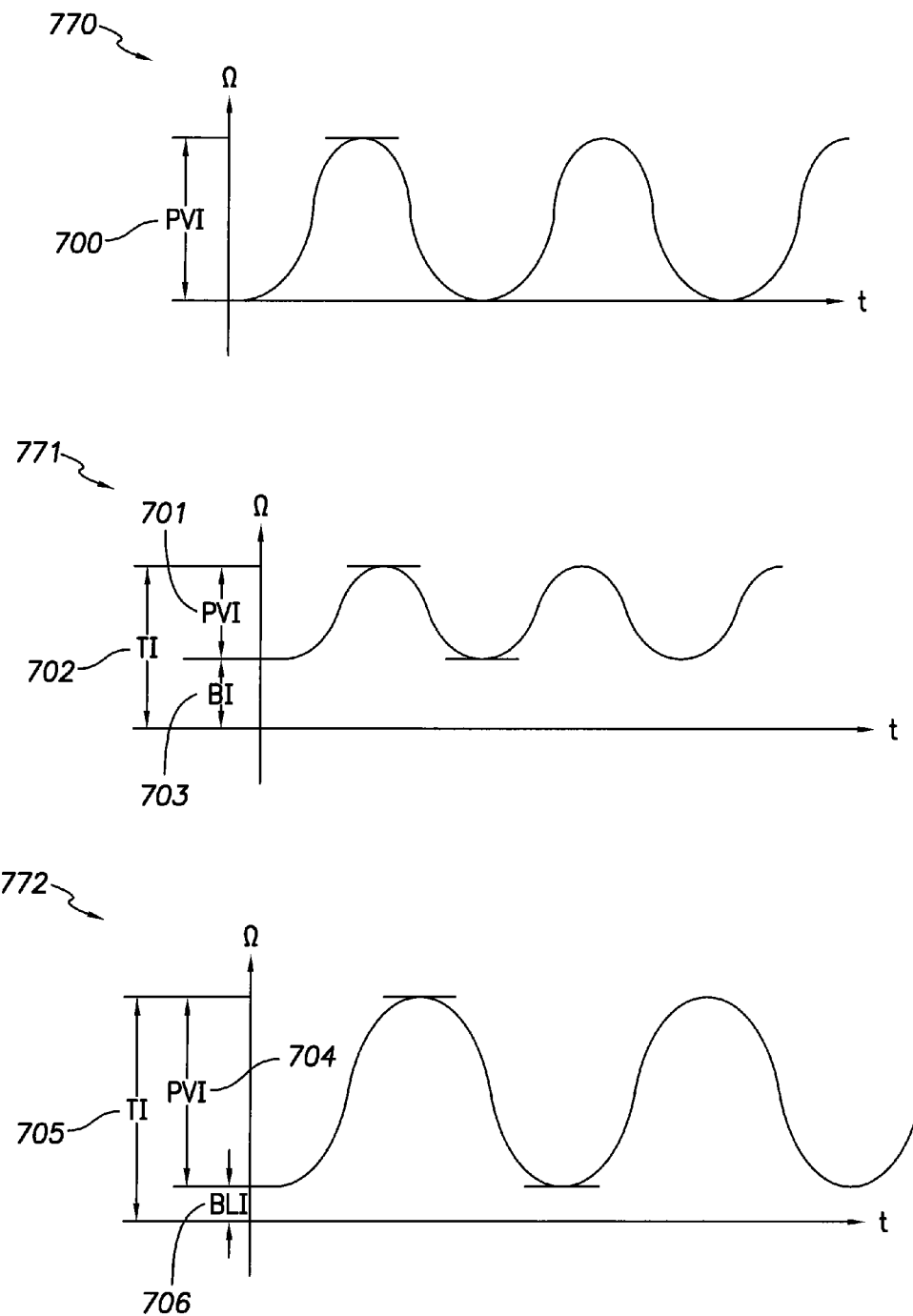
FIG. 7 illustrates graphs of three resulting impedance measurements for the three test AV delay rates used in an AV optimization feature configured according to one embodiment of the present teachings.

FIG. 7 illustrates graphs of three resulting impedance measurements for the three test AV delay rates used in an AV optimization feature configured according to one embodiment of the present teachings. The impedance graph 770 represents the impedance measurement taken when the heart is being paced at a first of the three test AV delay rates identified in the AV delay chart 550 (FIG. 5). When an AV optimization feature analyzes the impedance graph 770, it observes the peak-to-valley impedance, PVI 700, to determine the level of stroke volume, which provides a measurement of the cardiac output of the heart.

The impedance graph 771 represents the impedance measurements for a second of the three test AV delay rates. When analyzing the performance of the second test AV delay rate, the optimization feature determines that the total impedance, TI 702, is roughly the same as the PVI 700. However, the TI 702 is made up of the PVI 701 and a baseline impedance, BI 703, which represents a constant impedance that remains from cycle to cycle. A baseline impedance may be caused by fluid that remains in the ventricle, which could be the result of the ventricle failing to empty sufficiently because of a sub-optimal AV rate. Compared to the stroke volume suggested by the PVI 700, the stroke volume suggested by the PVI 701 is much less. Therefore, the cardiac output produced when pacing the heart at the second AV delay rate is less than the output when pacing at the first AV delay rate.

The impedance graph 772 represents the impedance measurements for a third of the three test AV delay rates. When analyzing the performance of the third test AV delay rate, the optimization feature determines the total impedance, TI 705, to be greater than the total impedance of the impedance graph 770, PVI 700. However, the PVI 704 of the heart pacing at the third test AV delay rate is the same as the PVI 700. The TI 705 is greater because the heart experiences a BLI 706 which adds to the total ohmic measurement of the impedance in the impedance graph 772. Therefore, while the heart at both the first and third test AV delay rates maintain a similar cardiac output, something related to the heart being paced at the third test AV delay rate is triggering measurement of the BLI 706. The AV optimization feature would, thus, select the first AV delay rate as the optimal AV delay because the overall cardiac output and function of the heart when paced at the first AV delay rate is better. In general terms, the AV optimization feature using cardiac impedance to measure cardiac output would select the test AV delay rate that results in an impedance having the maximum peak-to-valley amplitude and having the lowest baseline impedance.

In an additional and/or alternative embodiment of the present teachings, thermodilution may be used to measure stroke volume and, therefore, some form of cardiac output. The thermal probe 200 (FIG. 2B) provides the hardware and circuitry to take such measurements. The thermal probe 200 includes two separate parts, a heating/cooling element (for example at a tip of the LV or RV lead) and a temperature sensor. Again, with reference to the present teachings, when an IMD detects a patient's heart rate is within the target rate boundary for AV delay optimization, cardiac output, through stroke volume, is measured during the pacing at each of the different test AV delay rates using thermodilution. In thermodilution, a heating/cooling element, such as the heating/cooling element of the thermal probe 200 (FIG. 2B), modifies the temperature of blood in the chamber to a given temperature, e.g., 32° C., 34° C., 40° C., 45° C., or the like. A temperature sensor, such as the temperature sensor of the thermal probe 200, measures the temperature of the blood in the chamber. When the temperature reaches the desired level, the heating/cooling element turns off and the temperature sensor continues to monitor the temperature of the blood in the chamber. A full thermodilution cycle is complete when the blood reaches the desired temperature and then returns to its normal temperature.

Figure 8:
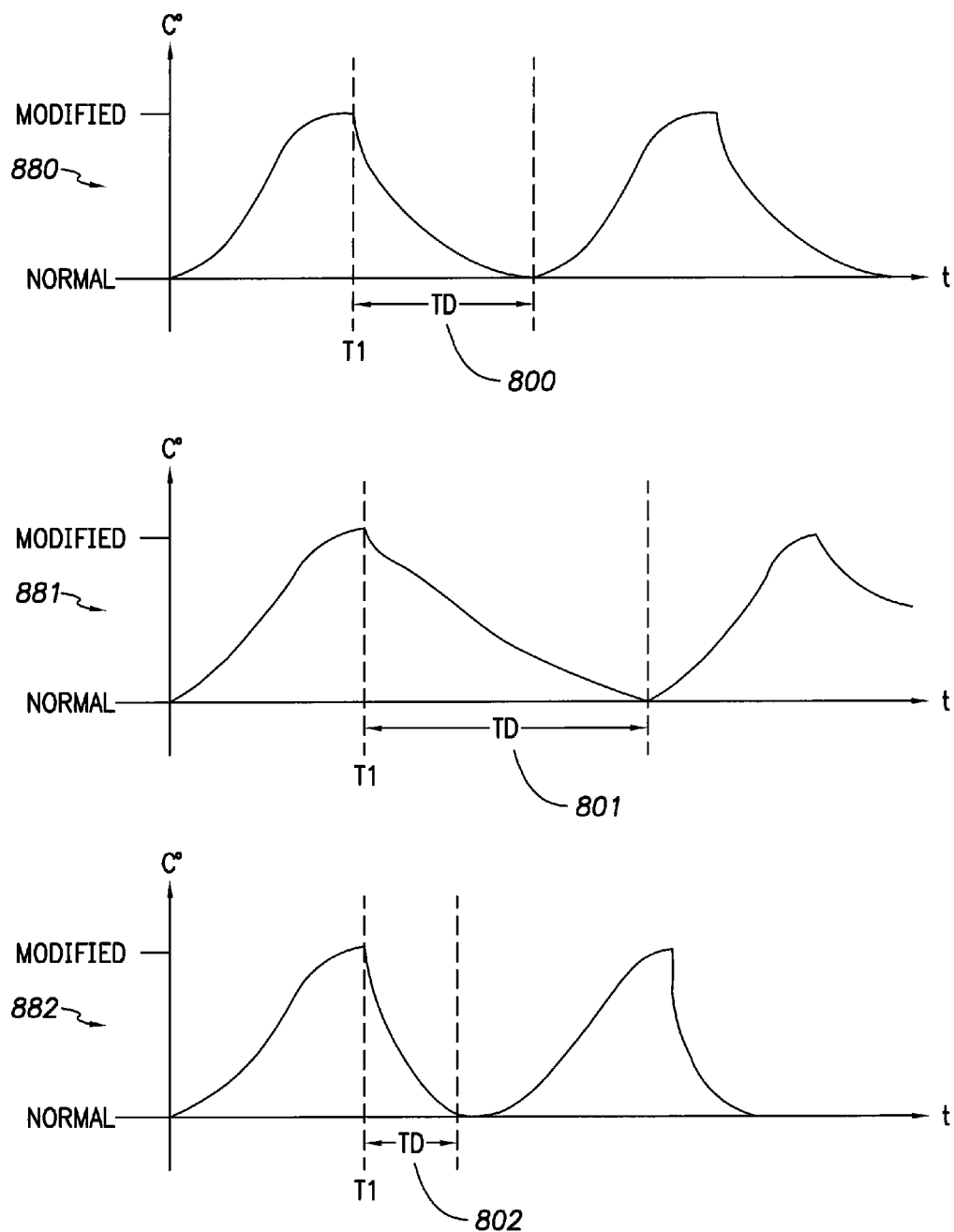
FIG. 8 illustrates graphs of three resulting thermodilution measurements for the three test AV delay rates used in an AV optimization feature configured according to one embodiment of the present teachings.

FIG. 8 illustrates graphs of three resulting thermodilution measurements for the three test AV delay rates used in an AV optimization feature configured according to one embodiment of the present teachings. A thermodilution graph 880 represents the temperature measurements during successive thermodilution cycles of the heart while being paced at the first of three test AV delay rates identified in the AV delay chart 550 (FIG. 5). The area of interest in each thermodilution cycle is the temperature decay, TD 800, which reflects the amount of time the blood takes to return to its normal temperature when the desired modified temperature is reached at time, T1. The greater the blood flow, i.e., the stroke volume/cardiac output, the faster the blood will return to it normal temperature and the shorter the thermal decay will be.

The thermodilution graph 881 represents the temperature measurements during the successive thermodilution cycles of the heart while being paced at the second of three AV delay rates. Here, the TD 801 is much longer than the TD 800, which suggests that the stroke volume produced when the heart is paced at the second test AV delay rate is much less than the stroke volume produced using the first test AV delay rate.

The thermodilution graph 882 represents the temperature measurements during the successive thermodilution cycles of the heart while being paced at the third of three AV delay rates. In this third test case, the TD 802 is shorter than the TD 800. Therefore, when each of the temperature measurements of the thermodilution graphs 880-882 is analyzed by the AV optimization feature, it will select the third test AV delay rate as the optimum AV delay because it produced the shortest thermal decay, TD 802, and, thus, the highest stroke volume.

In an additional and/or alternative embodiment of the present teachings, blood pressure may be used to measure stroke volume and, therefore, some form of cardiac output. The pressure sensor 201 (FIG. 2C) provides the hardware and circuitry to take such measurements. Again, with reference to the present teachings, when an IMD detects a patient's heart rate is within the target rate boundary for AV delay optimization, cardiac output, through stroke volume, is measured during the pacing at each of the different test AV delay rates using blood pressure.

Figure 9:
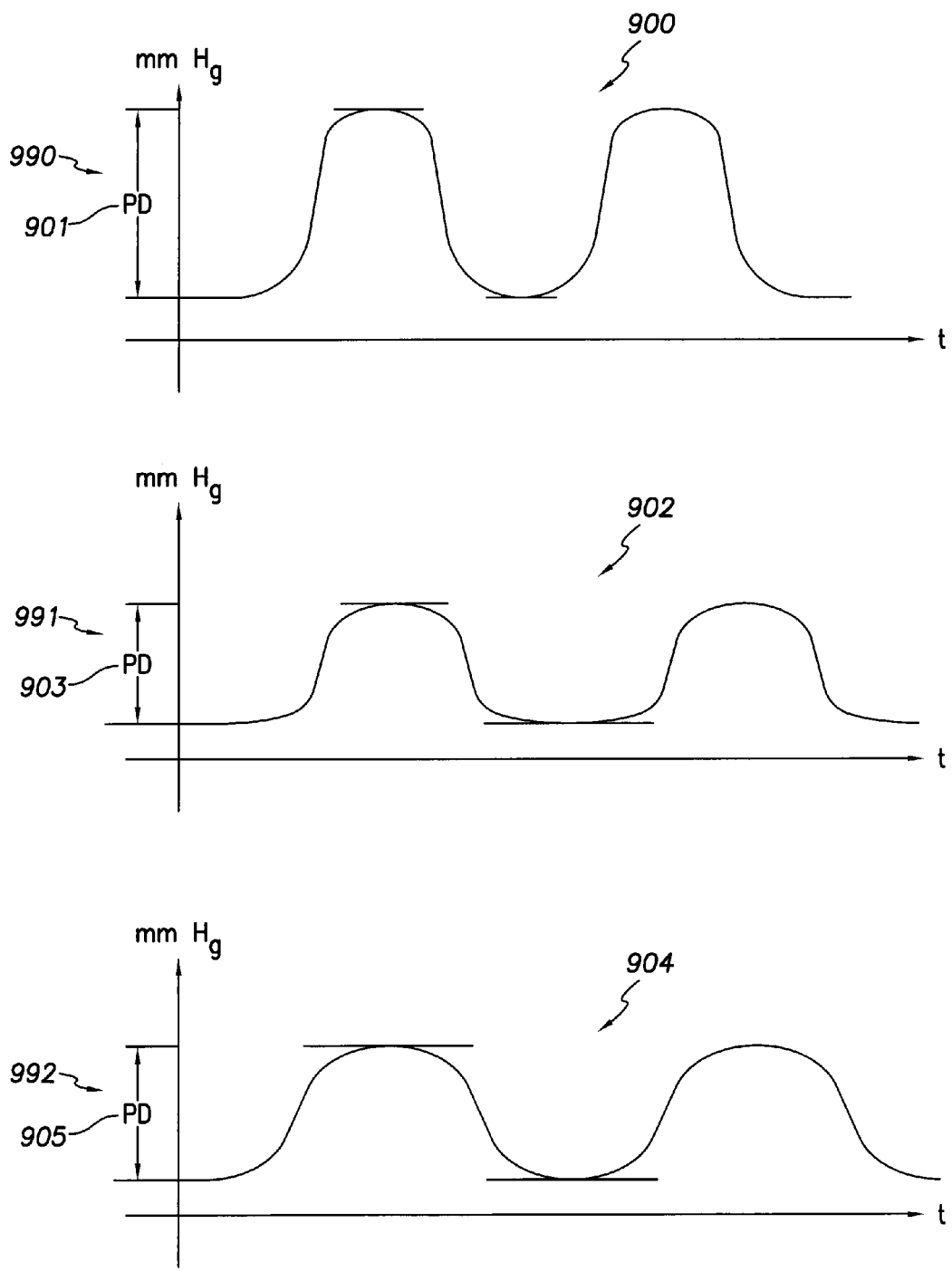
FIG. 9 illustrates graphs of three resulting continuous blood pressure measurements for the three test AV delay rates used in an AV optimization feature configured according to one embodiment of the present teachings.

FIG. 9 illustrates graphs of three resulting continuous blood pressure measurements for the three test AV delay rates used in an AV optimization feature configured according to one embodiment of the present teachings. A blood pressure graph 990 represents the continuous blood pressure measurements while pacing the heart using the first of three test AV delay rates identified in the AV delay chart 550 (FIG. 5). A peak to valley pressure value, PD 901, is determined in a blood pressure waveform 900. A large peak to valley pressure value will typically represent a higher stroke volume, excluding any hypertensive blood pressure measurements. Similar to the AV optimization analysis conducted using cardiac impedance, the pressure analysis is a peak-to-valley measurement. Therefore, when analyzing the blood pressure measurements, the AV optimization feature will select the largest peak to valley pressure value as representing the highest stroke volume performance.

The blood pressure graph 991 represents the continuous blood pressure measurements taken while pacing the heart using the second of three test AV delay rates. A peak to valley pressure value, PD 903, is determined in a blood pressure waveform 902. Here, the PD 903 is smaller than the PD 901, which suggests that the stroke volume produced when the heart is paced at the second test AV delay rate is less than the stroke volume produced using the first test AV delay rate.

The blood pressure graph 992 represents the continuous blood pressure measurements while pacing the heart using the third of three test AV delay rates. A peak to valley pressure value, PD 905, is determined in a blood pressure waveform 904. Here, the PD 905 is also smaller than the PD 901, which suggests that the stroke volume produced when the heart is paced at the third test AV delay rate is also less than the stroke volume produced using the first test AV delay rate. Therefore, the AV optimization feature, after comparing the peak to valley pressure values reflected in the blood pressure graphs 990-992, would select the first test AV delay rate as the optimal AV delay and store that optimal AV delay in an optimal AV delay table along with its corresponding heart rate.

In another embodiment, a differential of the pressure with respect to time (i.e., dp/dt) is analyzed. If the pressure sensor is within the left ventricle, then the left ventricle dp/dt is the surrogate for the cardiac output. If noise obscures the pressure signal being analyzed, then the maximum value of dp/dt can act as the surrogate.

With regard to the determination of cardiac output using the aortic arch flow surrogates described in FIGS. 7-9, testing of the three different test AV delay rates was generally described. It should be noted that, in practice, testing of the multiple, different AV delay rates would not occur sequentially. That is, the various embodiments of the present teachings would not test the lowest AV delay rate immediately followed by the next lowest AV delay rate immediately followed again by the next lowest AV delay rate. Employing such a sequential method would likely cause the testing of the AV delay rates to be skewed slightly based on the gradual performance memory exhibited by the heart. If the heart is not allowed first to return to a standard or substantially different AV delay prior to testing the next higher AV delay rate, the performance of the heart will be influenced by the immediately-preceding AV delay rate due to a gradual performance memory experienced by the heart at incrementally increasing AV delay rates. Instead, options may be exercised that place a pacing pause, i.e., a period of time in which the heart is paced at a standard AV delay rate, between each of the test AV delay rates. Additionally, the testing sequence may be "randomized," such that the testing sequence does not progress directly from lower to medium to high AV delay rates. This randomized sequence would prevent the gradual performance memory experienced in the direct low-to-high testing sequence.

Figure 10:
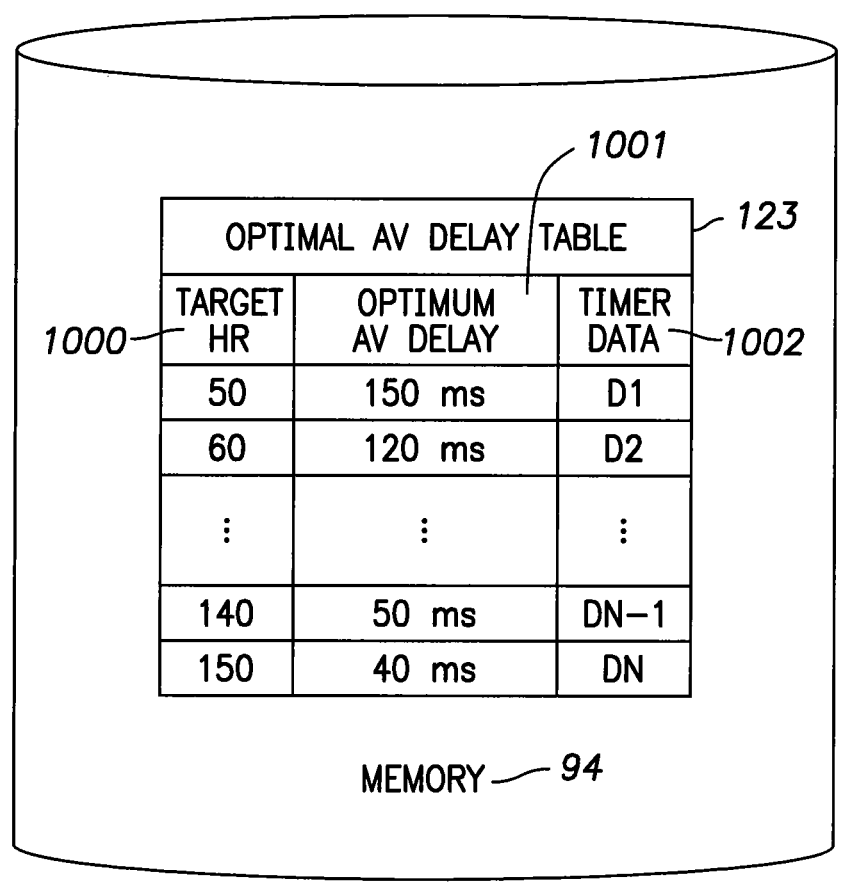
FIG. 10 is a block diagram illustrating details of the optimal AV delay table stored on a memory of an implantable stimulation device and configured according to one embodiment of the present teachings.

Turning now to FIG. 10, a block diagram is shown illustrating details of the optimal AV delay table 123 stored on the memory 94 and configured according to one embodiment of the present teachings. The optimal AV delay table 123 maintains a target heart rate list 1000 that includes each of the heart rates that fall within the target rate boundary generated for the individual patient. As the AV delay optimization process unfolds, the AV optimization feature stores selected optimal AV delay rates in an optimal AV delay list 1001. The optimal AV delay table 123 is configured as a relational data structure in which the AV delay stored in the optimal AV delay list 1001 corresponds to a particular heart rate in the target heart rate list 1000. In addition to storing and relating the target heart rate and its corresponding optimal AV delay, the optimal AV delay table 123 also includes a timer data list 1002 which stores timing information, D1-DN, related to the selected AV delays in the optimal AV delay list 1001. The timing information D1-DN provides a "staleness" indication with regard to the selected AV delays.

Over time, the physiology of a patient's heart will change, whether the change is due to an improved condition, a temporary illness, or simple time-related degeneration. Because of this inevitable change, optimal AV delay rates selected in one period will cease to be optimal after the passage of time, i.e., when the stored optimal AV delay rate exceeds a certain, predetermined age. For this reason, timing information D1-DN provides a clock for the IMD with an AV optimization feature configured according to one embodiment of the present teachings to update AV delay selections. The timing information D1-DN may take any number of various forms. For example, it may be a simple date stamp noting the date on which the selection was made. After a predefined time has passed since that date, the AV optimization feature will place that target heart rate on the optimization rotation once again. The timing information D1-DN may also be a counter value, where the value is incremented or decremented after the passage of a defined period (e.g., day, number of hours, or the like). When the counter is either counted down to zero or counted up to a predefined maximum, the associated target heart rate is again placed into the optimization rotation. Therefore, the timing information D1-DN allows for the optimal AV delay rates to remain optimal over the course of treatment for each patient.

The methodologies described herein may be implemented by various means depending upon the application. For example, these methodologies may be implemented in hardware, firmware, software, or any combination thereof. For a hardware implementation, the processing units, including programmable microcontroller 60 (FIG. 2A) may be implemented within one or more application specific integrated circuits (ASICs), digital signal processors (DSPs), digital signal processing devices (DSPDs), programmable logic devices (PLDs), field programmable gate arrays (FPGAs), processors, controllers, microcontrollers, microprocessors, electronic devices, other electronic units designed to perform the functions described herein, or a combination thereof. For a firmware and/or software implementation, the methodologies may be implemented with modules (e.g., procedures, functions, and so on) that perform the functions described herein. Any machine or computer readable medium tangibly embodying instructions that may be in a form implantable or coupled to an IMD may be used in implementing the methodologies described herein. For example, software code may be stored in a memory and executed by a processor. When executed by the processor, the executing software code generates the operational environment that implements the various methodologies and functionalities of the different aspects of the teachings presented herein. Memory may be implemented within the processor or external to the processor. As used herein the term "memory" refers to any type of long term, short term, volatile, nonvolatile, or other memory and is not to be limited to any particular type of memory or number of memories, or type of media upon which memory is stored. The machine or computer readable medium that stores the software code defining the methodologies and functions described herein includes physical computer storage media. A storage medium may be any available medium that can be accessed by the processor of an IMD. By way of example, and not limitation, such computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. As used herein, disk and/or disc includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer readable media.

Although the present teachings and its advantages have been described in detail, it should be understood that various changes, substitutions and alterations can be made herein without departing from the spirit and scope of the present teachings as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present teachings, processes, machines, manufacture, compositions of matter, means, methods, or steps, presently existing or later to be developed that perform substantially the same function or achieve substantially the same result as the corresponding embodiments described herein may be utilized according to the present teachings. Accordingly, the appended claims are intended to include within their scope such processes, machines, manufacture, compositions of matter, means, methods, or steps.

What is claimed is:

1. A method for optimizing atrioventricular (AV) delay in elevated heart rates, said method comprising:
measuring a heart rate from an implantable medical device (IMD);
responsive to said heart rate falling within a target range of elevated heart rates, pacing a heart by said IMD using a plurality of AV delays, wherein each of said plurality of AV delays is different than another of said plurality of AV delays;
measuring a cardiac output of said heart during said pacing at each of said plurality of AV delays wherein measuring the cardiac output comprises determining aortic arch blood flow;
selecting an optimal AV delay of said plurality of AV delays, wherein said optimal AV delay corresponds to one of said plurality of AV delays producing a highest cardiac output; and storing said optimal AV delay and said heart rate in an optimal AV delay table on said IMD.

2. The method of claim 1 wherein said determining said aortic arch blood flow comprises at least one of:
measuring a cardiac impedance;
measuring a thermodilution response; and
measuring a blood pressure.

3. The method of claim 2 wherein said determining said aortic arch blood flow comprises said measuring said cardiac impedance, wherein said selecting said optimal AV delay comprises:
comparing a peak-to-valley value in a measured impedance waveform for each of said plurality of AV delays during said pacing; and
comparing a baseline impedance in said measured impedance waveform for each of said plurality of AV delays, wherein said highest cardiac output corresponds to a largest one of said peak-to-valley values having a lowest of said baseline impedance.

4. The method of claim 3, in which the cardiac impedance is measured between an SVC coil electrode and a housing of the IMD.

5. The method of claim 2 wherein said determining said aortic arch blood flow comprises varying a temperature of blood within a heart chamber from a first temperature to a second temperature, and determining a length of time until the blood returns to the first temperature, wherein said selecting said optimal AV delay comprises:
comparing the length of time for each of said plurality of AV delays, wherein said highest cardiac output corresponds to a shortest one of the lengths of time.

6. The method of claim 2 wherein said determining said aortic arch blood flow comprises measuring said blood pressure, wherein said selecting said optimal AV delay comprises:
comparing a peak-to-valley pressure value in a measured blood pressure waveform for each of said plurality of AV delays during said pacing, wherein said highest cardiac output corresponds to a largest one of said peak-to-valley pressure values.

7. An implantable medical device (IMD) comprising:
a heart rate sensor;
at least one cardiac pacing lead;
at least one cardiac output sensor;
a programmable microcontroller coupled to said heart rate sensor, to said at least one cardiac pacing lead, and to said at least one cardiac output sensor, wherein said programmable microcontroller controls operation of said IMD;
a memory coupled to said programmable microcontroller;
an atrioventricular (AV) delay optimization feature module stored on said memory, wherein, when executed by said programmable microcontroller, said AV delay optimization feature module configures said IMD:
to measure a heart rate of a heart associated with said IMD;
to operate, responsive to said heart rate falling within a target range of elevated heart rates stored in an optimal AV table on said memory, said at least one cardiac pacing lead to pace said heart using a plurality of AV delays, wherein each of said AV delays is different than another of said plurality of AV delays;
to operate said at least one cardiac output sensor to measure a cardiac output of said heart during said pacing at each of said plurality of AV delays by determining aortic arch blood flow values at each of the plurality of AV delays;
to select an optimal AV delay of said plurality of AV delays, wherein said optimal AV delay corresponds to one of said plurality of AV delays producing a highest cardiac output; and
to store said optimal AV delay in said optimal AV table associated with said heart rate.

8. The IMD of claim 7 wherein said at least one cardiac output sensor comprises at least one of:
an impedance measuring circuit;
a thermal probe; and
a pressure sensor.

9. The IMD of claim 8 wherein said at least one cardiac output sensor comprises said impedance measuring circuit, wherein said configuration of said IMD by said executing AV optimization feature module to operate said at least one cardiac output sensors comprises:
configuration to activate said impedance measuring circuit to measure cardiac impedance during pacing at each of said plurality of AV delays.

10. The IMD of claim 9 wherein said executing AV optimization feature module further configures said IMD:
to compare a peak-to-valley value in a waveform of said measured cardiac impedance of each of said plurality of AV delays during said pacing; and
to compare a baseline impedance in said waveform, wherein said highest cardiac output corresponds to a largest one of said peak-to-valley values having a lowest of said baseline impedance.

11. The IMD of claim 8 wherein said at least one cardiac output sensor comprises said thermal probe, wherein said configuration of said IMD by said executing AV optimization feature module to operate said at least one cardiac output sensors comprises:
configuration to activate said thermal probe to modify a temperature of blood within a heart chamber to a selected temperature different than a normal temperature of said blood during pacing at each of said plurality of AV delays; and
configuration to record a length of time from a beginning of said modification of said temperature until said blood returns to said normal temperature; and
configuration to compare a thermodilution response in a waveform of said recorded time measurements for each of said plurality of AV delays, wherein said highest cardiac output corresponds to a shortest one of said thermodilution responses.

12. The IMD of claim 8 wherein said at least one cardiac output sensor comprises said pressure sensor, wherein said configuration of said IMD by said executing AV optimization feature module to operate said at least one cardiac output sensors comprises:
configuration to activate said pressure sensor to measure blood pressure during pacing at each of said plurality of AV delays.

13. The IMD of claim 12 wherein said executing AV optimization feature module further configures said IMD:
to compare a peak-to-valley pressure value in a waveform of said measured blood pressure for each of said plurality of AV delays during said pacing, wherein said highest cardiac output corresponds to a largest one of said peak-to-valley pressure values.

14. The IMD of claim 8 wherein said at least one cardiac output sensor comprises said pressure sensor, wherein said configuration of said IMD by said executing AV optimization feature module to operate said at least one cardiac output sensors comprises:

configuration to activate said pressure sensor to measure blood pressure during pacing at each of said plurality of AV delays and to determine a maximum differential value of the pressure with respect to time.

15. The IMD of claim 7 wherein said executing AV optimization feature module further configures said IMD:

to store timing information related to said selected optimal AV delay, wherein, when said timing information indicates said selected optimal AV delay is beyond a predetermined age, a new optimal AV delay is selected when said heart rate falls into said target range of elevated heart rates again.

16. A system that optimizes atrioventricular (AV) delay in elevated heart rates, said system comprising:

means for measuring a heart rate from an implantable medical device (IMD);

means, executable responsive to said heart rate falling within a target range of elevated heart rates, for pacing a heart by said IMD using a plurality of AV delays, wherein each of said plurality of AV delays is different from another of said plurality of AV delays;

means for measuring a cardiac output of said heart during said pacing at each of said plurality of AV delays comprising means for determining aortic arch blood flow;

means for selecting an optimal AV delay of said plurality of AV delays, wherein said optimal AV delay corresponds to one of said plurality of AV delays producing a highest cardiac output; and means for storing said optimal AV delay and said heart rate in an optimal AV delay table on said IMD.

17. The system of claim 16 wherein said means for measuring cardiac output comprises at least one of:

means for measuring a cardiac impedance;

means for measuring a thermodilution response; and means for measuring a blood pressure.

18. The system of claim 17 wherein said means for measuring cardiac output comprises said means for measuring said cardiac impedance, wherein said means for selecting said optimal AV delay comprises:

means for comparing a peak-to-valley value in a measured impedance waveform for each of said plurality of AV delays during said pacing; and means for comparing a baseline impedance in said measured impedance waveform for each of said plurality of AV delays, wherein said highest cardiac output corresponds to a largest one of said peak-to-valley values having a lowest of said baseline impedance.

19. The system of claim 17 wherein said means for measuring cardiac output comprises said means for measuring said thermodilution response, wherein said means for selecting said optimal AV delay comprises:

means for comparing said thermodilution response in a measured temperature waveform for each of said plurality of AV delays, wherein said highest cardiac output corresponds to a shortest one of said thermodilution responses.

20. The system of claim 17 wherein said means for measuring cardiac output comprises said means for measuring said blood pressure, wherein said means for selecting said optimal AV delay comprises:

means for comparing a peak-to-valley pressure value in a measured blood pressure waveform for each of said plurality of AV delays during said pacing, wherein said highest cardiac output corresponds to a largest one of said peak-to-valley pressure values.

* * * * *